(12) United States Patent
Woods et al.

(10) Patent No.: US 11,966,876 B2
(45) Date of Patent: Apr. 23, 2024

(54) FACILITY AND METHOD OF USE FOR A TRANSPORTABLE AUTONOMOUS ROBOTIC MERCHANDISE DISPENSING DRIVE-THRU

(71) Applicants: Ray F Woods, Salem, OH (US); Rachel K Woods, Salem, OH (US)

(72) Inventors: Ray F Woods, Salem, OH (US); Rachel K Woods, Salem, OH (US)

(73) Assignee: Ray F. Woods, Salem, OH (US)

( * ) Notice: Subject to any disclaimer, the term of this patent is extended or adjusted under 35 U.S.C. 154(b) by 549 days.

(21) Appl. No.: 17/235,981

(22) Filed: Apr. 21, 2021

(65) Prior Publication Data

US 2022/0343263 A1 Oct. 27, 2022

(51) Int. Cl.
| | |
|---|---|
| G06Q 10/087 | (2023.01) |
| A47J 36/32 | (2006.01) |
| A47J 44/00 | (2006.01) |
| A61L 2/10 | (2006.01) |
| B60P 3/025 | (2006.01) |
| E04H 3/04 | (2006.01) |
| F25D 13/06 | (2006.01) |
| G05B 19/4155 | (2006.01) |
| G06K 7/10 | (2006.01) |
| G06Q 20/20 | (2012.01) |
| G06Q 50/12 | (2012.01) |

(52) U.S. Cl.
CPC .......... *G06Q 10/087* (2013.01); *A47J 36/321* (2018.08); *A61L 2/10* (2013.01); *B60P 3/0257* (2013.01); *F25D 13/06* (2013.01); *G05B 19/4155* (2013.01); *G06K 7/1095* (2013.01); *G06Q 20/209* (2013.01); *A47J 44/00* (2013.01); *A61L 2202/11* (2013.01); *A61L 2202/122* (2013.01); *A61L 2202/14* (2013.01); *A61L 2202/17* (2013.01); *E04H 3/04* (2013.01); *G05B 2219/50391* (2013.01); *G06Q 50/12* (2013.01)

(58) Field of Classification Search
CPC .... G06Q 10/087; G06Q 20/209; G06Q 50/12; A47J 36/321; B60P 3/0257; E04H 3/04
See application file for complete search history.

(56) References Cited

U.S. PATENT DOCUMENTS

| | | | |
|---|---|---|---|
| 9,098,954 B1 * | 8/2015 | Byrd | G01S 3/04 |
| 2018/0127192 A1 * | 5/2018 | Cohen | G07F 13/06 |
| 2018/0158153 A1 * | 6/2018 | Ekin | B60P 3/0257 |

(Continued)

OTHER PUBLICATIONS

Meyer, Christopher, Automatic Multiple Chamber Programmable Cooking Device, 2005, The Cooper Union for the Advancement of Science and Art ProQuest Dissertations (Year: 2005).*

*Primary Examiner* — Allen C Chein
*Assistant Examiner* — Aaron N Tutor

(57) ABSTRACT

The present invention is a transportable autonomous robotic merchandise dispensing drive thru wherein merchandise is loaded into said facility and dispensed to a customer through an ordering app downloaded on a mobile device or ordered at a facility site. Said drive thru facility is unmanned and completely computer and robotically operated utilizing no humans within said facility. Said facility is operated via computer processor and requires internet but no utility connections such as water, sewage, electric or gas. The current invention has a three part sanitizing system: interiorly, in each serving compartment and at each exterior touchscreen.

14 Claims, 3 Drawing Sheets

(56) References Cited

U.S. PATENT DOCUMENTS

| | | | | |
|---|---|---|---|---|
| 2019/0299835 A1* | 10/2019 | Taylor | ............... | B60P 3/0257 |
| 2019/0311445 A1* | 10/2019 | Werner | ............... | G06Q 50/12 |
| 2020/0017014 A1* | 1/2020 | Lopez | ............... | B60P 3/0257 |
| 2020/0146496 A1* | 5/2020 | Patadia | ............... | A47J 36/321 |
| 2021/0022559 A1* | 1/2021 | Zito | ............... | A47J 44/00 |
| 2022/0145613 A1* | 5/2022 | Haynes | ............... | B62D 27/02 |
| 2023/0042650 A1* | 2/2023 | Ross | ............... | G05D 1/0221 |

* cited by examiner

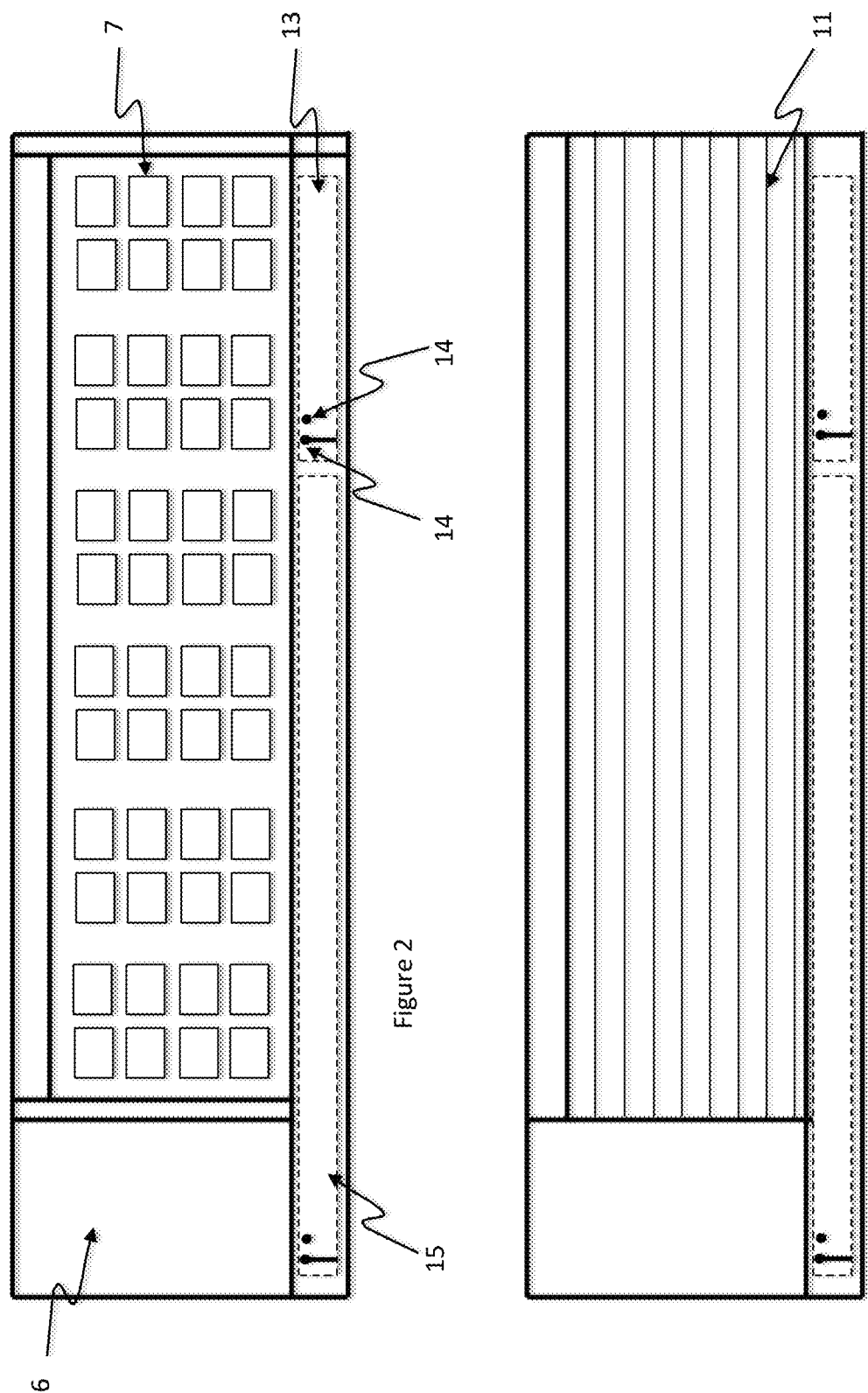

FACILITY AND METHOD OF USE FOR A TRANSPORTABLE AUTONOMOUS ROBOTIC MERCHANDISE DISPENSING DRIVE-THRU

CROSS-REFERENCE TO RELATED APPLICATIONS

This application claims priority from U.S. Provisional Patent Application No. 62/704,105 filed Apr. 21, 2020 with the United States Patent and Trademark Office. The disclosure of which is incorporated herein.

BACKGROUND

1. Field

The present invention relates to a drive-thru where a customer's order is taken through a speaker or in person and the customer does not leave their vehicle while their order is paid for, prepared and served. The present invention relates to vending machines as well. Vending machines are pre-loaded with merchandise and a customer can chose an item to purchase and the machine produces the purchased item to the customer. Vending machines are autonomous and don't require an employee to accept payment, select, prepare or package selected merchandise.

2. Description of Related Art

Drive-thru restaurants also known as quick service restaurants (QSR) have long provided many people through out the world with hot, ready to eat meals ordered, paid for, and picked up all while the customer remains in their vehicle. With a majority of both parents working, children's extra-curricular activities, and long work hours; people choose to pick up a meal on the go from a QSR in order to feed themselves and families. In general, QSRs are fairly inexpensive with meals cooked to order but are not always the healthiest option for nourishment due to time restraints. Many menu items are fried, full of saturated fats, sugars and preservatives; pre-cooked processed foods can be heated quickly enabling a QSR to serve orders within minutes. QSR's present many problems beyond lack of healthy nourishment, for instance; most QSR's require multiple employees to take orders and payment as well as prepare and package foods and beverages. Time is of the essence in drive-thrus, orders made through a two-way speaker (intercom) can be entered into the computer or prepared incorrectly which can create longer wait times for customers and sometimes another trip around the drive thru. As with all human involvement comes human error, which results in unhappy and impatient customers. Among other problems presented by QSR's are the necessity for property, large investment for the building, and accessible utilities, supplies, multiple employees willing to work for minimal wages (which leads to absenteeism, causing franchises to be short staffed), not to mention that employees who work with food on an everyday basis do not always follow hygiene proto-calls put in place to keep customers from getting sick by ingesting contaminated foods and beverages. The entire floor plan for some QSR's are laid out so that employees are able to perform duties in an assembly line format as well as providing the public dining areas and restroom facilities. The footprint and requirements for a public dining area in a QSR require additional capital, space, utilities and employees. Employees are responsible for more than 35% of cost incurred by QSR's. Drive-thru franchises are subject to population density in a given geographical area in order to support costs incurred to run the QSR. This limits where and how many franchise QSR's are located within an area. Potential customers in rural areas do not have the privilege of enjoying ready-made food due to low population within a certain geographical area. Rural residents must travel to a QSR and are less likely to indulge than those residents that are in a closer proximity to a chosen QSR. Among the aforementioned problematic issues with the conventional QSRs, additional issues include improper cooking device cleaning, untimely replacement of oils required for deep-frying foods causing fowl tasting fried food products, and easy transmission of communicable diseases due to human on human contact.

Vending machines offer merchandise for sale but do not require an associate to prepare, serve or package said merchandise. An item chosen from a vending machine is dispensed in the same condition it was purchased. If the item is cold when purchased, it is dispensed from the vending machine cold. For example, a customer purchases a cold sandwich from a vending machine, if the customer wants the sandwich heated then he/she must heat the sandwich themselves. Vending machines do not prepare, cook, or package merchandise and a majority of foods and beverages sold from vending machines are pre-cooked or highly processed, which is considered an unhealthy food. Occasionally, purchased merchandise may become hung up within a vending machine or said vending machine might malfunction leaving the customer without money spent or merchandise. This is problematic because vending machines are generally stocked on a weekly or bi-weekly schedule and more than likely the employee who restocks the vending machine is not present to refund money or correct the malfunction until the scheduled delivery. There is no communication between the vending machine and said delivery employee until the employee arrives for restocking. Another problem presented by related art vending machines is that inventory needed isn't known until the delivery employee arrives at the vending machine's location. This problem can lead to lost sales if an item is sold out. Without communication between a vending machine and an owner, theft is a potential problem. The delivery employee usually collects money from the vending machine as well as restocking it; and inventory is reported by said delivery employee where the owner relies upon the delivery employee to be honest. Yet another problem with vending machines is expired stock, usually pulled by a delivery employee, but can easily be overlooked and sold to a customer.

Please see published US patent applications 20200074440 titled "Methods and Systems for Autonomous Dispensing of Products", 20200053839 titled "Smart Packaging Systems and Methods", 20200051012 titled "System and Method for Managing the Delivery of a Food Product" and application 20200034848 titled "Drive-thru Based Order Processing Method and Apparatus". Also see U.S. Pat. No. 10,614,413 titled "Inventory Management System and Method of Use" and U.S. Pat. No. 10,617,321 titled "Methods and System for Food Ordering" These applications and patents are related art to the current invention, solving similar problems to those presented above but do not provide the solutions for problems in the food industry as aforementioned. After acknowledging prior art and related art it is desirable to present an automated drive-thru that is unmanned during operational hours and only requires delivery and pickup of foods and beverages from outside the facility. All listed problems pertaining to prior art are addressed and solved with the present invention.

BRIEF SUMMARY OF THE INVENTION

The current invention solves the aforementioned problems presented by prior art quick service restaurants, drive-thrus and vending machines by removing a majority of human involvement, presenting a communicably connected facility with a streamline design that does not require accessible utilities or an abundant population in a given geographical area, and providing a transportable autonomous robotic merchandise dispensing drive thru facility that is computerized and robotically run to achieve orders exactly how they were ordered and ready to be picked up or delivered at the exact time quoted. Merchandise, food and beverage portions are always the same and/or cooked exactly as ordered. The current invention provides an app for smartphones or computers for ordering as well as drive up or walk-up ordering from a touch-screen. There are no employees within a transportable autonomous robotic merchandise dispensing drive thru facility thus eliminating human error, issues due to employee absenteeism and transmission of communicable diseases. With the current invention, 35% of cost is saved and reinvested into quality healthy food options at comparable prices to prior art QSRs. Pre-ordering allows for a wider variety of menu options including meals that take longer to cook than prior art QSR or drive-thru menu options. The current invention dispenses merchandise including but not limited to foods and beverages, non food items, medications, toiletries, and various household items.

A transportable autonomous robotic merchandise dispensing drive thru facility can be set up in rural areas that have no access to sewage, water and electric or gas. Said facilities are portable and come equipped with solar panels, generators that have the ability to utilize used cooking grease as fuel and an energy-saving magnetic method of cooking. The current invention contains a large compartment of potable water used to make beverages and perform a daily cleaning and sanitizing of each facility. Grey water (waste-water) is drained into a separate compartment and stored until pumped out with a delivery truck. Delivery trucks can be equipped with refrigerated compartments where food-containing lockers are stored until delivered. Restocking a transportable autonomous robotic merchandise dispensing drive thru facility is streamline and simple. Each item is counted, recorded, attached to an individual product code and stored in an air tight computerized box. A merchandise locker is exchanged with previously loaded lockers at said facility site; right out of the truck, where the product code is scanned as a particular item and recorded within the computer system of the transportable autonomous robotic merchandise dispensing drive thru facility. Particular details such as temperature and quantity etc. are exchanged within the facility's computer system interface. Communications between the transportable autonomous robotic merchandise dispensing drive thru facility, delivery drivers, and customers will be further explained in the "detailed description of the invention" section.

The transportable autonomous robotic merchandise dispensing drive thru facility can be utilized by schools, churches, hospitals, job sites, FEMA relief efforts, third world countries and eventually in individual homes where merchandise is ordered and prepared at a given time and quantity. By eliminating direct human contact during merchandise selection, food prep, cooking and packaging, said facility provides clean, healthy, precisely cooked meals or undamaged merchandise without the worry of contracting an illness or inability to staff and run a QSR kitchen, home kitchen or otherwise merchandise retail facility. The current invention has the ability to be placed in locations where prior art QSRs could not exist due to population density, land and building cost, available utilities, space and amenities required to work the public or seat customers.

BRIEF DESCRIPTION OF THE SEVERAL VIEWS OF DRAWINGS

FIG. 2 is a side view of said facility's merchandise lockers with exterior door open.

FIG. 3 is an alternative view of FIG. 2 with said exterior door closed.

DETAILED DESCRIPTION OF THE INVENTION

Figure 1:
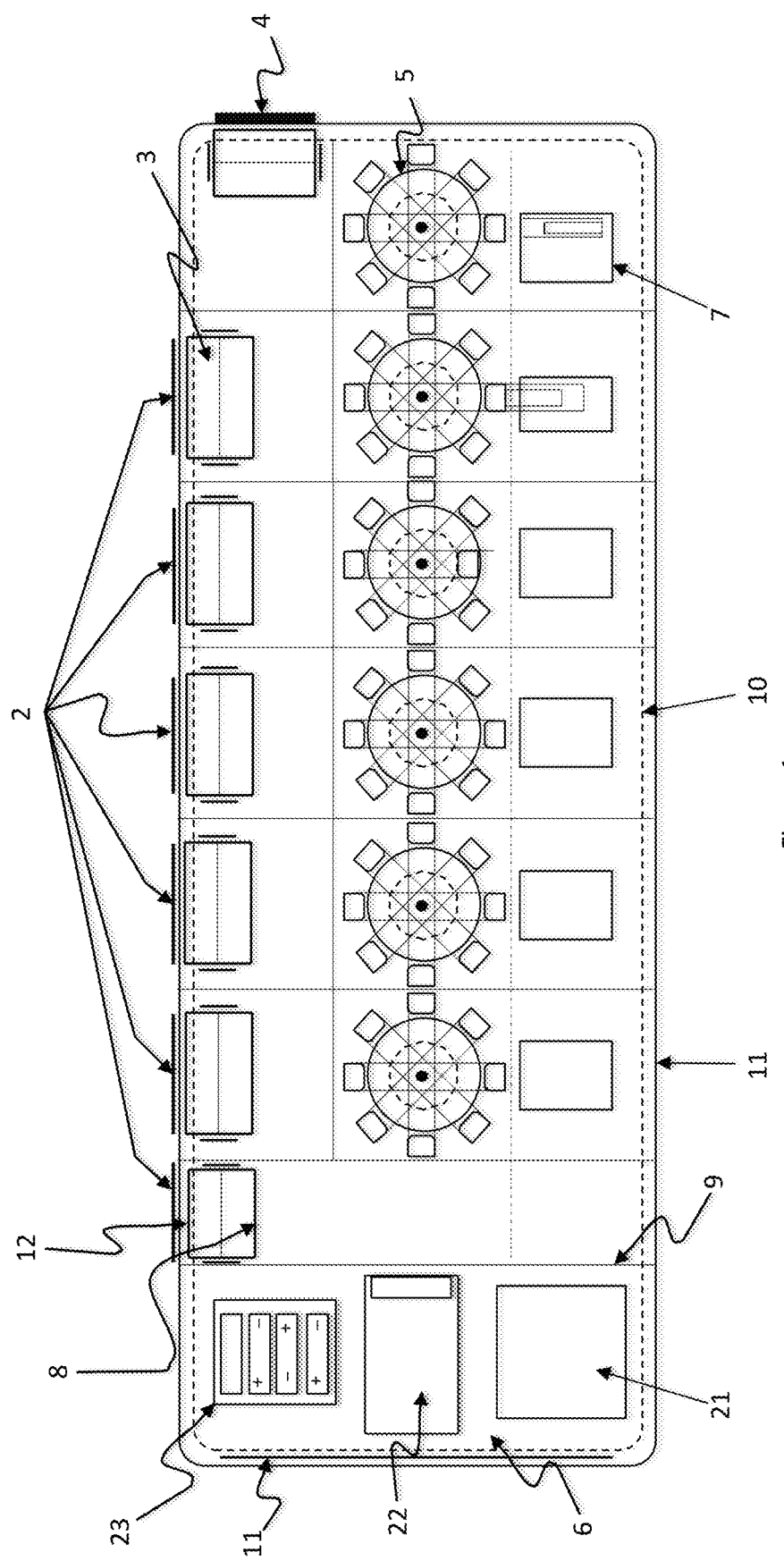
FIG. 1 is a sectional view of some components in a transportable autonomous robotic merchandise dispensing drive thru facility.

The current invention is a transportable autonomous robotic merchandise dispensing drive thru facility, as seen in FIG. 1, that is an unmanned facility and has the capability of same day relocation. The transportable autonomous robotic merchandise dispensing drive thru solves issues presented by QSR franchises including problems with employees such as; employee absenteeism, improper hand washing, spread of communicable diseases, cost associated with facility requirements to accommodate employees ie. floor space, heating and cooling, restroom facilities etc., human error when taking or making an order, added cost for insurance, wages, worker compensation etc. as well as employee theft. When human involvement is limited to outside a QSR facility, the potential for errors on an order fall drastically. A transportable autonomous robotic merchandise dispensing drive thru facility will be manufactured on an assembly line and once completed will be transported to a desired location to serve customers hot ready-to-eat meals, various beverages and otherwise merchandise. The cost associated with building a new QSR franchise or remodeling an older one is sharply decreased for several reasons. Approximately a quarter of the square footage of land required for a conventional QSR is all that is needed for a transportable autonomous robotic merchandise dispensing drive thru facility. Said facility is completely computerized and robotically run, no human presence is required so the floor plan is compact and all square feet are usable space. The compact design and interior finished surfaces are commercial and not used by the public or employees thus saving cost in employee insurance, finished floors, tvs, tables, chairs, restrooms, sinks, soaps, lighting, wages, square footage, employee theft, wasted food and beverage products to name a few. By eliminating cost, you gain a transportable autonomous robotic merchandise dispensing drive thru that will remain open 23 hours a day (allowing an hour for facility shutdown and cleaning) 365 days a year, through storms, shutdowns, strikes, and pandemics as long as a transportable autonomous robotic merchandise dispensing drive thru is kept supplied, its' computer and robotics run the merchandise prepping, cooking, packaging, orders, payments, cook times, inventory and cleaning. Additional cost savings include utility hookups required; including but not limited to water, sewage, electric or gas. Each transportable autonomous robotic merchandise dispensing drive thru can be equipped with solar panels, a battery bank 23, a generator 22 and a potable water compartment 15 as well as a separate grey water compartment 13.

The current invention is run by a computer processor 21 designed to communicate with a customer preferably through an app downloaded by the customer via internet connection with a mobile device, tablet etc or through a walk up window 4 with touchscreen 24. Upon ordering off the merchandise menu and processing payment via credit/debit card or cash, the customer will receive an order number/code either to their mobile device, personal computing device etc or in paper form if ordering from designated walkup window 4 with touchscreen 24. The customer will also be quoted an exact time and drive thru window 2 number to pickup the order. To retrieve the order, the customer drives up to a designated drive thru window 2 or walk up window 4 with a touchscreen 24 secured to the facility adjacent said window, each touchscreen 24 is equipped with a scanner where said customer scans the code received at time of purchase. The transportable autonomous robotic merchandise dispensing drive thru computer 21 then signals a robotic retrieval arm to locate the meal attached to the scanned code and delivers it to the window where the customer scanned his/her code. When the order arrives at said window a first door closes behind a compartment where said order was positioned and a second exterior serving compartment door 12 opens for the customer to remove their order. After the customer has retrieved their order, the second exterior serving compartment door 12 closes and a built in UV light sanitizes all surfaces, within the serving compartment 3 that were accessible to the customer. Interior walls, bottom and ceiling of said serving compartment 3 are constructed to flip and receive a washing/sanitizing to remove any food debris that may have been left behind leaving the serving compartment 3 clean and dry. This small but important sanitizing step will greatly reduce the spread of communicable diseases by customers of the transportable autonomous robotic merchandise dispensing drive thru.

The transportable autonomous robotic merchandise dispensing drive thru facility is comprised of at least four exterior walls, a ceiling structure and a floor structure. As seen in FIG. 1 a utility compartment 6 is located in a first end of said facility. Said utility compartment 6 has at least one air and water tight interior wall 9 separating it from a merchandise storage compartment 10, packaging storage compartment and any cooking device 5. Said utility compartment 6 contains a generator 22, a battery bank 23, and a computer operating system 21. Said merchandise storage compartment 10 is located along one of two exterior walls intersecting with said utility compartment interior wall 9. The merchandise storage compartment 10 is accessible through at least one merchandise loading door 11 that is situated in said exterior wall parallel and adjacent to said merchandise storage compartment 10. Said merchandise storage compartment 10 can be set at a favorable temperature suitable for storing merchandise until purchased, cooked and/or packaged for a customer. Within said food/merchandise storage compartment 10 is an electronic rack unit utilized for storing a particular product stored within said merchandise lockers 7 or packaging material lockers. Said merchandise lockers 7 and packaging material lockers are electronic and store product sensitive information such as quantity, temperature, expiration, merchandise product code and locker location. As a merchandise locker 7 or packaging material locker is loaded in said electronic rack, said product sensitive information is passed from said merchandise locker 7 to the electronic rack and sent to said facility's computer operating system 21. Merchandise lockers 7 and packaging material lockers can be manufactured in cylindrical or box shapes, whichever best suits each product. Opposite and parallel to said merchandise storage compartment 10 exterior wall is an exterior wall with multiple drive thru windows 2. Each drive thru window 2 is equipped with a touchscreen and scanner. Said windows each have a mechanically and computer operated exterior door utilized for a customer to retrieve an order. A customer flashes a code received on their mobile device under the scanner, with no need to touch the touchscreen, the scanner then signals the facility's operating system which intern signals a robotic conveying system to retrieve said order and deliver the order to said drive thru window's 2 interior door of a serving compartment 3 where a robotic arm indexes and pushes the order into a serving compartment 3 and where said serving compartment interior door 8 closes and said order is contained between said serving compartment interior door 8 and a serving compartment exterior door 12. The serving compartment exterior door 12 then opens and the customer is able to retrieve their order without having to exchange money, credit/debit cards, air or physical contact with another human thus lowering a likely hood of passing bacteria, virus or a communicable disease. After a customer retrieves their order, the serving compartment exterior door 12 closes and the serving compartment interior door 8 is closed encasing a serving compartment, where a UV light is used to kill any bacteria within the serving compartment 3. When food debris is sensed within the serving compartment 3 all walls, bottom and top of said serving compartment 3 flip and are washed/sanitized from outside of the serving compartment 3, removing any and all food debris.

Located in a second end of said facility, opposite and parallel the utility compartment 6, is a walk-up order window 4 used for ordering while paying with cash/debit card or cash without the use of the customer app where the customer will receive an order number/code in the form of a paper receipt. Said walk-up customer will pick up their order from the walk-up window 4. Said walk-up window 4 has a touchscreen with scanner as well as a cash-accepting device. All touchscreens are sanitized by a UV light after each customer uses them.

Located between the merchandise storage compartment 10 and said exterior wall with drive thru windows 2 can be cooking (frying, baking, deep frying, and warming) devices 5, packaging materials, packaging devices, conveyors (utilized for moving individual products or to complete orders) and beverage making devices. Each transportable autonomous robotic merchandise dispensing drive thru facility can have a variety of menu choices including but not limited to beef, poultry, pork, fish, seafood, soups, hot and cold sandwiches, breakfast items (eggs, bacon, pancakes etc.) breads, vegetables, salads, drinks (hot or cold) soda, desserts (ice cream, cakes, pies, cookies, pastries etc), vegan, paleo and gluten-free foods and beverages and non-food items. In each transportable autonomous robotic merchandise dispensing drive thru facility, depending on a specific menu, cooking and packaging devices 5 will be arranged and stocked with foods, beverages, merchandise and packaging materials to suit said menu. Due to a wide variety of menu options, said cooking devices 5 and product retrieval devices can vary at each facility. Because combinations of cooking devices 5, chilling devices, beverage devices, condiment dispensing devices and packaging devices and materials are so numerous; an example of a couple different combinations of said devices and materials will be discussed hereinafter as well as a sequence of communications between customer, a customer app, a facility operating computer 21, robotic cooking and packaging devices 5, conveyors, merchandise hubs, delivery drivers, a service app and a corporate headquarters.

When an order is processed through a transportable autonomous robotic merchandise dispensing drive thru customer app, the transportable autonomous robotic merchandise dispensing drive thru computer 21 operating system processes said order based on preloaded parameters (example: cooking time, cooking temperature, cooking device, and merchandise locker placement for retrieval) based on said menu item. Said menu item, for example a chilled hamburger patty, is robotically indexed from designated merchandise locker and onto a frying device surface. Said item is cooked for a proper length of time and in the example of a hamburger, the hamburger is cooked from above and below by two heated surfaces to eliminate the process of flipping said hamburger. After the hamburger is cooked it is indexed onto a conveyor to receive any ordered toppings and condiments and moved into a robotic packaging station where said hamburger receives a wrapper and is packaged with any other warm food items ordered. Once an order is complete it is then loaded on a conveyor system with multiple individual platforms to hold said order's hot and cold items until the customer scans his/her code for pickup or until a predetermined time period has passed. As the order is placed on a platform of said conveyor, order information and the customer code is digitally attached to said platform. Upon retrieval of the order the digital information is then removed from said designated platform and recorded as processed and a new order can now be loaded on said platform. In the event an order is not picked up and remains on it's designated platform for longer than the predetermined period of time, the order information is processed by the facilities operating system as a discounted order for a predetermined period of time. The facilities computer 21 operating system will then load the order information onto a discounted order section on the customer app for that particular facility's location for all customers to see and purchase. If the discounted order is not repurchased within a predetermined time period, the order is then discarded within said facilities refuse to be compacted and stored until a delivery driver retrieves said refuse. Multiple customer orders can be processed and cooked simultaneously as each cooking device 5 has multiple independent cooking surfaces and each cooking device surface is electronically communicated with by said computer 21 operating system. Each cooking device 5 receives individual information based on a particular order until said food item is cooked and indexed to packaging station. At every stage of merchandise movement, from the time merchandise locker 7 are packaged at a merchandise hub to an order being picked up by a customer; the merchandise item product information, processing (cooking, packaging) information and order code is passed each time said merchandise item is moved within the transportable autonomous robotic merchandise dispensing drive thru, serving merchandise exactly as ordered and at the specific time quoted.

The transportable autonomous robotic merchandise dispensing drive thru customer application is downloaded on a mobile device by a customer. The application provides information such as said facility nearest the user. Once the user chooses the location of a given transportable autonomous robotic merchandise dispensing drive thru within the app, the menu for that particular location is loaded on the customer's mobile device screen as well as any specials or discounted food items/orders. Once the customer has entered their order, payment with a bank/savings account or credit/debit card is required to process the order. After payment is received through the customer app, the location of the transportable autonomous robotic merchandise dispensing drive thru chosen receives the order information and the customer receives an order code and time the order can be picked-up. All order information is recorded within said facility's computer 21 processor/operating system and is processed within the facility to produce the order as well as communicating with said facility's merchandise hub and corporate headquarters. A merchandise hub is a facility where merchandise items are packaged and stored within said merchandise lockers 7 to serve a number of transportable autonomous robotic merchandise dispensing drive thru facilities in a given geographic region. Each merchandise hub has a number of delivery drivers that are responsible for stocking each transportable autonomous robotic merchandise dispensing drive thru facility. Because all order information is communicated to said merchandise hub, inventory is easily tracked and restocked or exchanged if said merchandise item is expired or found to be contaminated. Each delivery driver has a transportable autonomous robotic merchandise dispensing drive thru service app on their mobile device communicating which merchandise items need replenished through a merchandise and packaging loading door 11 at each of the transportable autonomous robotic merchandise dispensing drive thru facilities they service. Delivery drivers are also responsible for replenishing merchandise including water and retrieving waste water and refuse from each facility they service, all such information is communicated to the driver through service app. The service app sends and receives digital information from each merchandise locker 7 whether its being taken out of said facility or installed, every item is scanned. Said service app communicates all information to said merchandise hub and said corporate headquarters. Each transportable autonomous robotic merchandise dispensing drive thru facility is in constant communication with a merchandise hub and corporate headquarters. In the event a facility encounters a mechanical problem, information is sent to a designated food hub and corporate headquarters and a technician is dispatched to correct the problem. If the problem requires the transportable autonomous robotic merchandise dispensing drive thru facility to shut down, said facility is taken off line and will not show up on the customer app until fixed and put back on line or another facility is brought to the location and exchanged with said problematic transportable autonomous robotic merchandise dispensing drive thru. Because the design of each transportable autonomous robotic merchandise dispensing drive thru facility is set up with multiple independent devices, a certain device may encounter a problem that does not affect the other devices within a said facility and may not be required to be taken off line to fix said problem. Should the problem encountered force the facility be taken offline, the technician can work on the facility on site or if it requires multiple hours of work, a different facility can easily and quickly be brought to the site and exchanged with the problematic facility. Then the problematic facility can be taken back to a manufacturing facility to be fixed and sent back out to a different location to be utilized and put back online.

Figure 4:
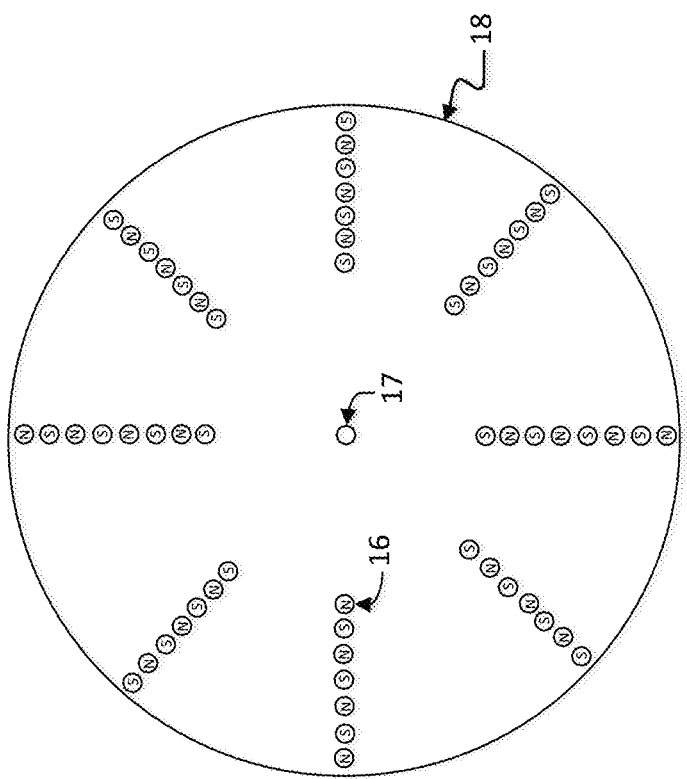
FIG. 4 illustrates the disc with attached magnets used to heat cooking devices.
Figure 5:
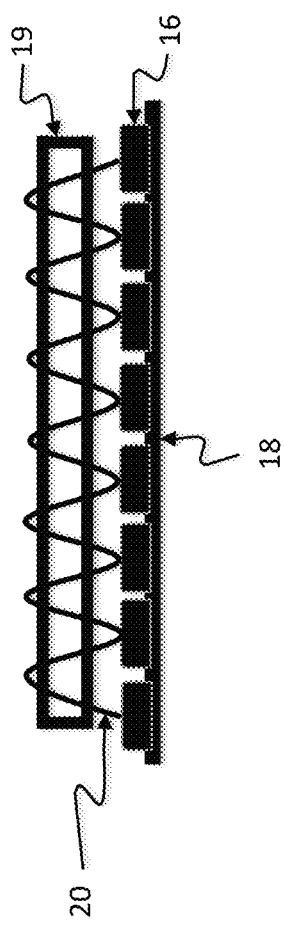
FIG. 5 depicts a magnetic field created by the arrangement of magnets in a North, South, North, South pole combination.

Each type of cooking device 5; frying, deep frying, baking or heating utilizes heat created by rotating magnets 16 arranged on a disc 18 in a plurality of circles with opposite poles facing the last magnet (North—N and South—S) creating a N S N S N S N S N pattern as seen in FIG. 4 and FIG. 5. As the magnets arranged in said circles are rotated at high RPM and placed near a copper surface 19, above and/or beneath, said copper surface 19 becomes glowing hot within seconds. The temperature of the copper surface 19 can be controlled by the speed the magnets 16 are rotated as well as the distance between the magnets 16 and the copper surface 19. There is very little energy lost due to friction in spinning the magnets 16 that are arranged on a disc 18 in a circle and where a bearing 17 is attached in a center of said disc 18 and said bearing 17 is attached to a shaft and the disc 18 and the magnets 16 do not come into contact with the copper surface 19. Therefore, little energy is required to create an abundant amount of heat for each cooking device 5. As the magnets 16 are rotated, the magnetic field 20 created causes the copper surface 19 to heat up as the magnets 16 remain cool to the touch. Where said magnets 16 remain cool to the touch, heat energy does not damage said magnets 16 enabling longevity of magnet 16 life.

In order to stop the spread of disease and bacteria, conventional QSRs require daily cleaning of cooking, prepping, packaging and beverage surfaces; normal tasks performed by employees if they do their job correctly. In a transportable autonomous robotic merchandise dispensing drive thru facility, a sanitizing and cleaning cycle is preformed daily. During said cleaning cycle, said facility goes into lockdown. During said lockdown, the facility shows on its app to be in a cleaning cycle and a time when it will be receiving new orders as the cleaning cycle is complete. Within a transportable autonomous robotic merchandise dispensing drive thru facility there are many cooking devices 5 and conveyers with surfaces that can come into contact with food or beverage items and all of them are located within an inner compartment of said facility. Said cooking devices 5 and conveyors' inner compartment is enclosed by the aforementioned merchandise storage compartment 10 and an inner wall where said serving compartment interior doors 8 are utilized to accept food orders. During the cleaning cycle the serving compartment interior doors 8 are sealed creating an air and water-tight wall, and where said merchandise storage compartment 10 wall is air and water-tight because all the merchandise lockers 7 are closed and locked down. All packaging materials used to cover merchandise are retracted and stored behind said inner wall with merchandise. After all inner walls and compartments are locked down, a cleaning cycle begins. Strategically placed sprayers begin a sanitizing procedure where any and all merchandise debris is blasted from all surfaces within the locked down compartment. Grey water and merchandise debris is rinsed from all surfaces and into a drain that is connected to a grey water storage compartment 13. Used grease can be strained and used as fuel to run the facility generator 22. A drying system then blows any remaining moisture from cooking devices 5 and conveyor surfaces. After said sanitizing and drying is complete, interior walls and windows unlock and the transportable autonomous robotic merchandise dispensing drive thru is ready to resume fulfilling orders. It is important to consumers to receive bacteria and virus free meals. The current invention is equipped with a three-part cleaning/sanitizing system, where all surfaces that come in contact with humans or merchandise, and/or food are sanitized and cleaned at least daily or as needed.

The invention claimed is:

1. A transportable autonomous robotic merchandise dispensing drive thru facility comprising:
   a computer processor, located in a utility compartment of said facility is configured to communicably connect sending and receiving data to and from a customer application, where said customer application is downloadable to a personal mobile device, and where said computer processor is configured to communicably connect transmit and receive information
   such as drive thru facility consumer orders, sales, inventory, temperature, operational details and predetermined merchandise storage temperatures, cooking and packaging parameters
   to a plurality of merchandise lockers, and packaging material lockers, one or more coolers, one or more freezers, one or more cooking devices, one or more beverage dispensing devices, one or more packaging devices, one or more conveying systems, one or more touchscreens each with a code scanner, a sanitizing and cleaning system, a merchandise distribution hub, a service application,
   where said service application is downloadable to a delivery driver's mobile device, and where said service application sends and receives inventory information and autonomous drive thru facility operational reports and where said service application communicably connects, sending and receiving information with corporate headquarters and each drive thru facility that is dedicated to each service driver,
   and said computer processor also communicably connects to a corporate headquarters, and where said computer processor receives data with order details from said customer application and generates a code per data received and where said code is linked to an order,
   and the computer processor issues instruction for one or more coolers and freezers, one or more merchandise lockers, one or more packaging material lockers, one or more cooking devices, one or more drink dispensing devices, one or more packaging devices, one or more conveying systems
   and where said code scanner reads an order code visible on a customer's mobile device and where said code reader communicates with the computer processor and the computer processor sends instruction to a robotic conveying system to retrieve an order linked to said code,
   and said computer processor receives data that said order was removed and sends instruction to said sanitizing system to sanitize a serving compartment;
   wherein said sanitizing system is three part:
      where a first part is a plurality of sprayers arranged throughout the interior of the facility but not in the utility compartment, one or more freezers, one or more coolers and not in the merchandise and packaging material locker areas and where said sanitizing system part is programmed to sanitize once per 24 hour period and where said facility's computer processor sends instruction for shut down to all cooking devices, beverage dispensing devices, conveying systems and packaging devices during the sanitizing cycle, and where said facility computer processor continues to receive orders and adds time to a customer pickup time, and where any water and/or debris resulting from said sanitizing cycle is drained into said grey water compartment, where a second part of said sanitizing system is a UV light in each serving compartment that sanitizes said serving compartment after each order is removed by a customer, and where a third part of said sanitizing system is a UV light located above each touchscreen and code scanner and where said UV light is run over the touchscreen and code scanner after each customer has used it;

and where said computer processor sends data containing inventory, order information and facility operational health to a merchandise distribution hub and corporate headquarters, and where said drive thru facility is pre-manufactured with various merchandise handling devices specific to such merchandise to prepare, package and serve said merchandise before said drive thru facility is transported and wherein said drive thru facility is transportable via vehicle hauling and where said drive thru facility is established at a desired location and said facility is mechanically fastened to a ground surface via anchors and where said facility is self-leveling and said facility is connected to a world wide web for remote information transmission, sending and receiving and where when said facility is connected to the world wide web and operational, no humans are required within said facility to operate, prepare, package, serve and clean said merchandise and said drive thru facility.

2. The transportable autonomous robotic merchandise dispensing drive thru facility of claim 1, wherein
a utility compartment contains a generator, a battery bank where said battery bank is linked to one or more solar panels and said computer processor
and where said utility compartment is isolated from all merchandise lockers, packaging material lockers, coolers, freezers, cooking devices, conveying systems, beverage dispensing devices, serving compartments, touchscreens and sanitizing/cleaning devices.

3. The transportable autonomous robotic merchandise dispensing drive thru facility of claim 1, wherein
an exterior wall contains one or more windows for drive thru customers to pick up an order
and where said window is sealed with a vertical sliding door
and where a serving compartment is located behind said sliding door
and where said serving compartment is completely enclosed
and where said serving compartment has an interior vertical sliding door
and where said serving compartment is sealed from an interior and an exterior of said facility when both sliding doors are in a closed position
and where at least one sanitizing sprayer is located on exterior said serving compartment
and where UV light sanitizer is used on said interior of the serving compartment every time an order is removed from said serving compartment after said exterior and interior sliding doors are closed.

4. The transportable autonomous robotic merchandise dispensing drive thru facility of claim 1, wherein
an exterior wall opposite and parallel to said exterior wall with one or more windows is comprised of one or more doors and where said doors are utilized to stock the facility with merchandise lockers and packaging material lockers
and where said lockers each are electronically programmable and record item specific data including but not limited to quantity, temperature, expiration date, a specific item identification code and location
and where said lockers are received by an electronic rack that reads locker content information and sends data to said computer processor
and where said electronic rack can be located within a cooler or freezer
and where said rack can be part of a conveying system for moving lockers within said facility
and where said lockers are loaded and removed at the exterior of the facility.

5. The transportable autonomous robotic merchandise dispensing drive thru facility of claim 1, wherein
a potable water compartment is located in a bottom of said facility
and where a separate grey water compartment is adjacent said potable water compartment
and where said sanitizing system drains into said grey water compartment
and where each potable and grey water compartments are accessible through respective openings on an outside of said facility and where potable and grey water can be pumped in or out of each compartment through said openings.

6. The transportable autonomous robotic merchandise dispensing drive thru facility of claim 1,
wherein said cooking devices are heated by rotating a disc with a plurality of magnets
and where said plurality of magnets are attached to the disc
and where said magnets are arranged in multiple circles around the disc so that poles are alternating NSNSNSNS
and where when the disc is rotated near a copper surface said magnets create a large magnetic field that heats said copper surface and where said disc and magnets remain cool.

7. The transportable autonomous robotic merchandise dispensing drive thru facility of claim 6, wherein said disc is rotated and heat created on the copper surface is controlled by a speed of rotation and distance between said copper surface and disc with attached magnets.

8. The transportable autonomous robotic merchandise dispensing drive thru facility of claim 3, wherein a touchscreen with a code scanner is attached to the exterior of said facility and located near each serving window with sliding door and where each touchscreen and code scanner are sanitized by a UV light after each use.

9. The transportable autonomous robotic merchandise dispensing drive thru facility of claim 1,
wherein a window is located on an end of said facility and said window is a walk up window
and where said walk up window has a touchscreen and code scanner next to said window and where an order can be entered at said walk up window
and where said walk up window has a sliding door and a serving compartment
and where said touchscreen is adapted to accept payment for an order in a form of cash or a debit/credit card
and where said touchscreen is adapted to produce and dispense an order code and pick up time on a paper ticket.

10. The transportable autonomous robotic merchandise dispensing drive thru facility of claim 2, wherein said facility is autonomous and does not require utility connection and where said facility supplies it's own energy via solar panels and grease collection for generator fuel.

11. The transportable autonomous robotic merchandise dispensing drive thru facility of claim 1, wherein aforementioned merchandise and packaging material lockers are sanitized, stocked with an item and sealed at a merchandise distribution hub and delivered sealed to said drive thru facility, and where said lockers are configured to dispense an item when instructed by said facility computer processor.

12. The transportable autonomous robotic merchandise dispensing drive thru facility of claim 1, wherein said facility computer processor is configured to receive a plurality of orders simultaneously and where instruction is sent to one or more merchandise lockers, one or more cooking devices, beverage dispensing devices, packaging devices and conveying systems, and where said facility computer processor sends a code with an order pickup time, and where cooking instruction and time required to perform each individual task to prepare an order are predetermined.

13. The transportable autonomous robotic merchandise dispensing drive thru facility of claim 1, wherein said facility is operated completely electronically and requires no employees internally to operate said facility and where any device or merchandise locker within said facility can be remotely controlled.

14. A method to communicably connect a transportable autonomous robotic merchandise dispensing drive thru computer processor, a corporate headquarters, a customer application,
  where said customer application is downloadable to a personal mobile device,
  and where said computer processor is configured to communicably connect transmit and receive information to a plurality of merchandise lockers,
    and packaging material lockers,
    one or more electronic racks,
    one or more coolers,
    one or more freezers,
    one or more cooking devices,
    one or more beverage dispensing devices,
    one or more packaging devices,
    one or more conveying systems,
    one or more touchscreens each with a code scanner,
    a sanitizing and cleaning system,
    a merchandise distribution hub,
    a service application, where said service application is downloadable to a delivery driver's mobile device,
  the method including:
  receiving an order through the customer application
  the computer processor issues an order code and pickup time that is sent back through the customer application, then
  instruction is issued to the merchandise lockers, one or more cooking devices, one or more beverage dispensing devices, one or more packaging devices, one or more conveying systems,
  and order code information is received at one or more touchscreens each with a code scanner,
  merchandise and packaging material locker send information including, but not limited to, inventory, item specifications, item location, item expiration and item temperature,
  information received by the computer processor regarding inventory is sent to a merchandise distribution hub and through the service application to a delivery driver's mobile device,
  and where the computer processor receives inventory specific information through the service application during delivery of lockers to a facility,
  inventory specific information is received to the computer processor as each merchandise and packaging material locker is loaded in the electronic rack,
  when an order code is read by a code scanner, order code information is received by the computer processor and instruction is issued to one or more conveying systems to retrieve the order received for that order code,
  and where data is received by the computer processor as an order is picked up and a door on a window closes, the computer processor issues instruction for sanitizing of a serving compartment and sanitizing of a touchscreen and code scanner,
and where after 23 hours of operation of said drive thru facility the computer processor issues instruction for a shut down during cleaning and sanitizing,
  communicating with one or more cooking devices, one or more beverage dispensing devices, one or more conveying systems and packaging devices for lockdown during sanitizing cycle,
  communication between the computer processor and each cooking device, beverage dispensing device, conveying system, sanitizing system, electronic rack, merchandise and packaging material lockers, touchscreens and code readers, generator, battery bank, solar panels, freezers, coolers,
  where data includes but is not limited to temperature, motion, instruction, location, operation error, humidity, quantity, device specific operation information, and liquid levels,
  wherein said sanitizing system is three part:
    where a first part is a plurality of sprayers arranged throughout the interior of the facility but not in the utility compartment, one or more freezers, one or more coolers and not in the merchandise and packaging material locker areas and where said sanitizing system part is programmed to sanitize once per 24 hour period and where said facility's computer processor sends instruction for shut down to all cooking devices, beverage dispensing devices, conveying systems and packaging devices during the sanitizing cycle, and where said facility computer processor continues to receive orders and adds time to a customer pickup time, and where any water and/or debris resulting from said sanitizing cycle is drained into said grey water compartment,
    where a second part of said sanitizing system is a UV light in each serving compartment that sanitizes said serving compartment after each order is removed by a customer,
    and where a third part of said sanitizing system is a UV light located above each touchscreen and code scanner and where said UV light is run over the touchscreen and code scanner after each customer has used it;
  and the computer processer sends information to a customer application to alter a menu of items when an operation error has been received by the computer processor from the aforementioned devices or systems when a shut down message is received by a device or system, and all data received or sent by the computer processor is sent to a corporate headquarters.

* * * * *

UNITED STATES PATENT AND TRADEMARK OFFICE
CERTIFICATE OF CORRECTION

PATENT NO. : 11,966,876 B2  
APPLICATION NO. : 17/235981  
DATED : April 23, 2024  
INVENTOR(S) : Ray F. Woods and Rachel K. Woods Page 1 of 1

It is certified that error appears in the above-identified patent and that said Letters Patent is hereby corrected as shown below:

On the Title Page

Insert this after Prior Publication Data:
--Related U.S. Application Data
Provisional application No. 62/704,105 filed on April 21, 2020--

Signed and Sealed this
Twenty-seventh Day of August, 2024

Katherine Kelly Vidal
*Director of the United States Patent and Trademark Office*